United States Patent [19]
Kieturakis et al.

[11] Patent Number: 5,464,403
[45] Date of Patent: Nov. 7, 1995

[54] PLACEMENT TOOL AND METHOD FOR LAPAROSCOPIC HERNIA REPAIR

[75] Inventors: Maciej J. Kieturakis, San Carlos; Kenneth H. Mollenauer, Santa Clara; Helmut L. Kayan, Redwood City, all of Calif.

[73] Assignee: General Surgical Innovations, Inc., Portola Valley, Calif.

[21] Appl. No.: 85,288

[22] Filed: Jun. 30, 1993

Related U.S. Application Data

[63] Continuation-in-part of Ser. No. 968,551, Oct. 29, 1992, abandoned.

[51] Int. Cl.[6] .................................................. A61B 19/00
[52] U.S. Cl. ........................... 606/1; 128/898; 606/151
[58] Field of Search ........................... 604/93, 104, 158, 604/166, 171; 606/1, 107, 108, 113, 127, 138, 147, 151–158, 170, 171, 213; 128/887, 898

[56] References Cited

U.S. PATENT DOCUMENTS

| | | | |
|---|---|---|---|
| 5,112,155 | 6/1992 | Eberbach | 606/213 |
| 5,116,357 | 5/1992 | Eberbach | 606/213 |
| 5,141,515 | 8/1992 | Eberbach | 606/213 |
| 5,176,692 | 1/1993 | Wilk et al. | 606/213 |
| 5,263,969 | 11/1993 | Phillips | 606/213 |
| 5,304,187 | 4/1994 | Green et al. | 606/151 |

*Primary Examiner*—Stephen C. Pellegrino
*Assistant Examiner*—Glenn K. Dawson
*Attorney, Agent, or Firm*—Flehr, Hohbach, Test, Albritton & Herbert

[57] ABSTRACT

A tool for the placement of a flexible sheet having first and second edges and a width between the edges in a laparoscopic procedure in a patient utilizing a cannula having a passage therein. The tool includes an elongate tubular assembly having proximal and distal extremities, and an elongate tubular member having a bore. A rod is disposed in the bore and terminates short of the distal extremity of the elongate tubular assembly. A rotatable member is secured to the proximal extremity of the rod. A handle is secured to the proximal extremity of the elongate tubular assembly and receives the rotatable member. The handle has at least one opening therein overlying the rotatable member for rotating the rotatable member and the rod carried thereby. A sleeve of the tubular assembly has a distal extremity which has an inside diameter substantially greater than the outside diameter of the rod to form an annular chamber. The distal extremity of the tubular assembly has a slot extending longitudinally which permits access to the annular chamber and the distal extremity of the rod. The distal extremity of the rod engages one edge of the sheet so that as the rod is rotated the sheet of mesh is wound about the rod in one direction and brought into and stored as a roll in the annular chamber.

20 Claims, 3 Drawing Sheets

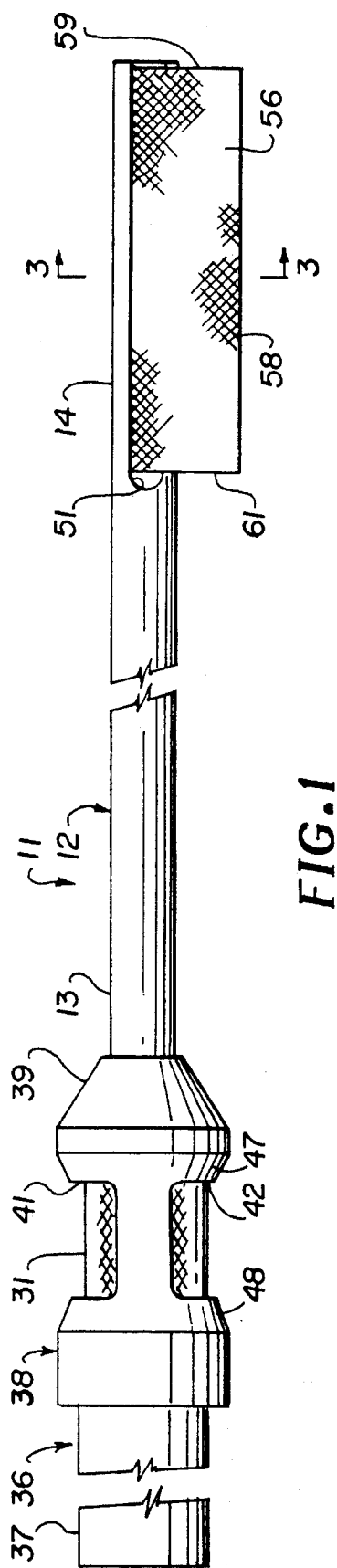
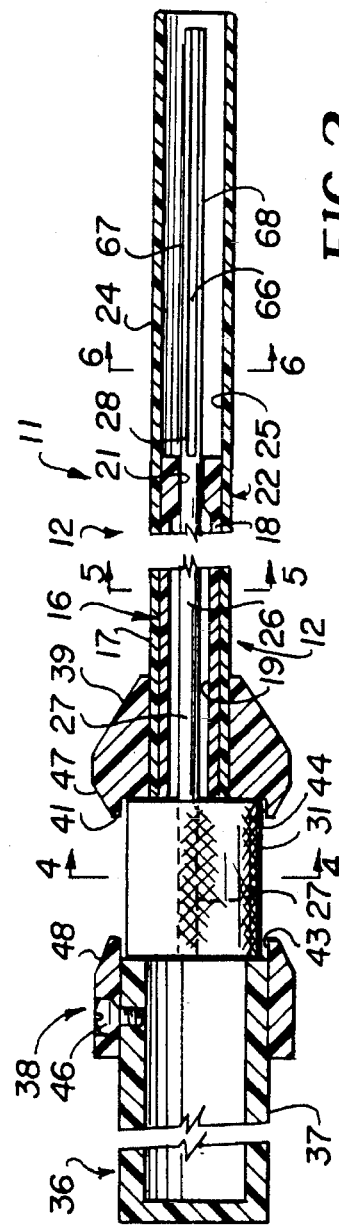
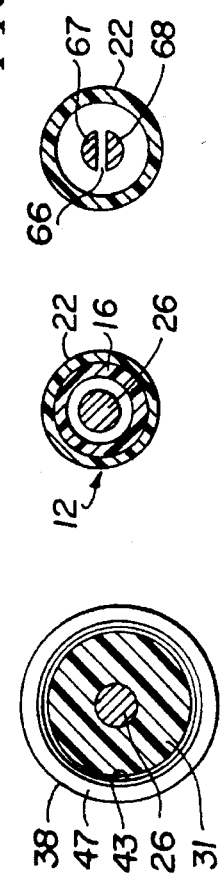
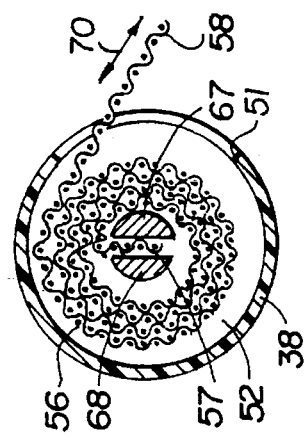
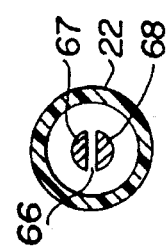
FIG.1  FIG.2  FIG.3  FIG.4  FIG.5  FIG.6

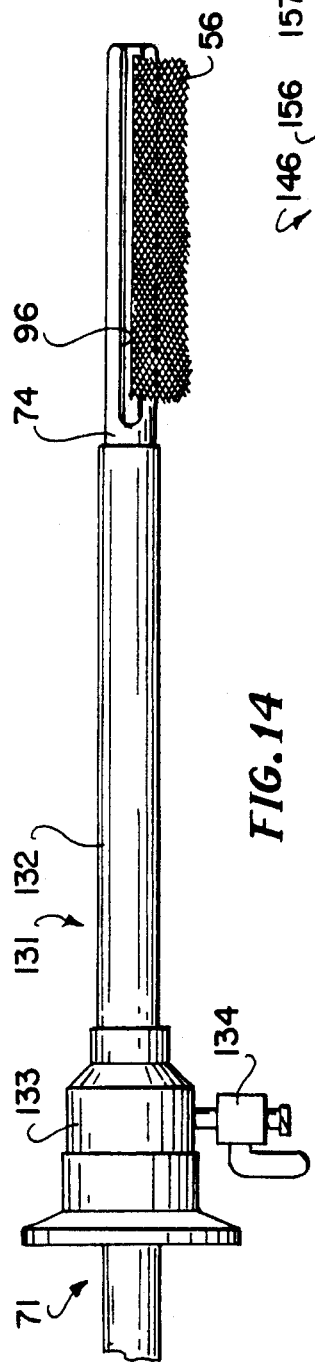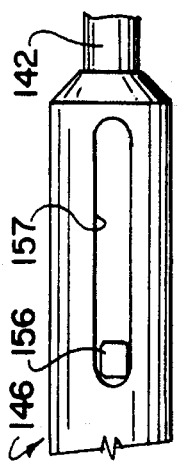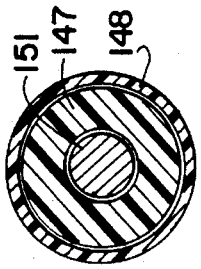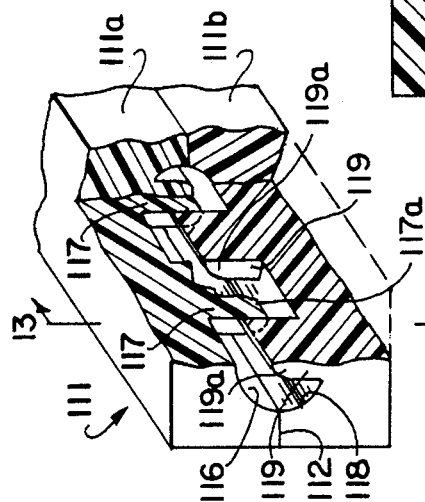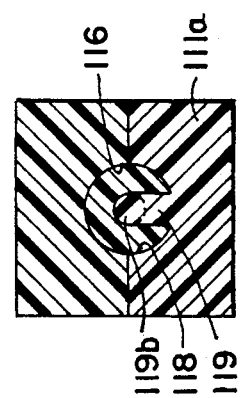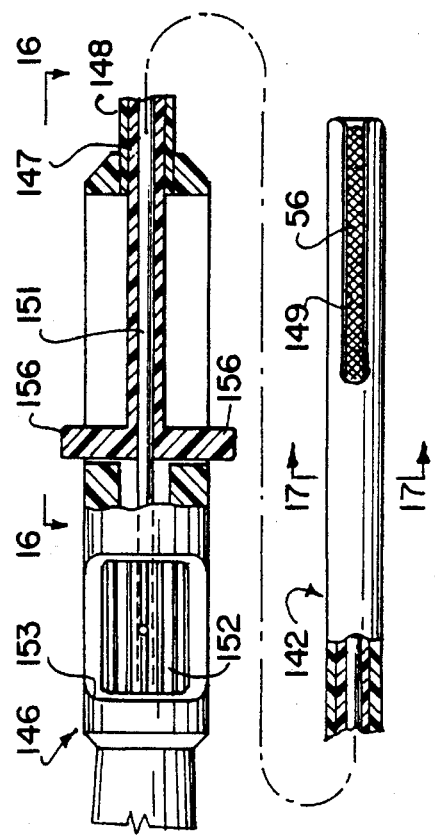

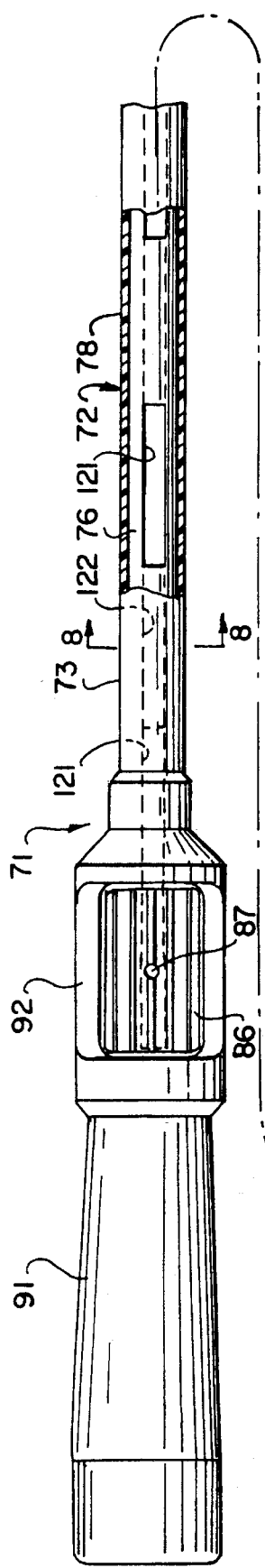
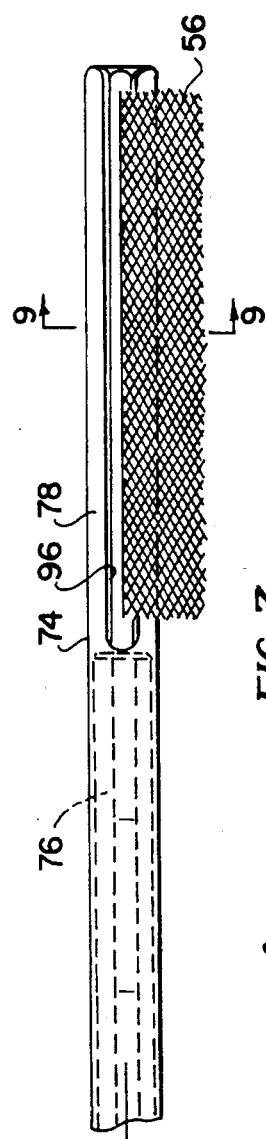
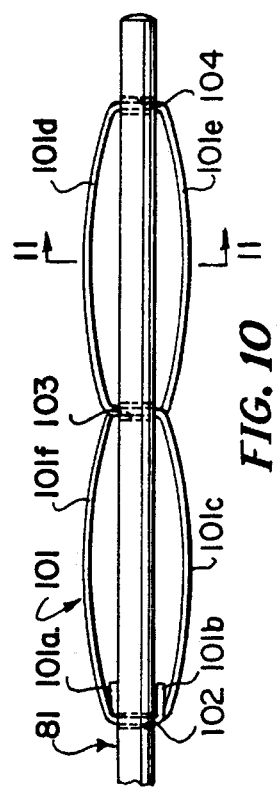
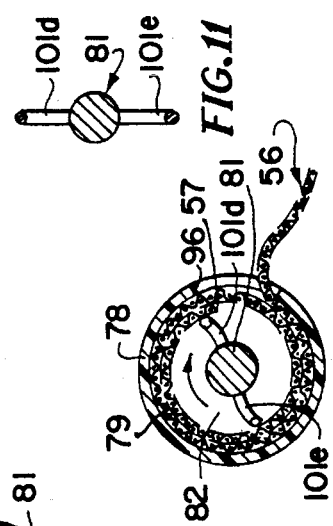
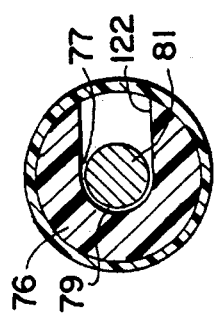
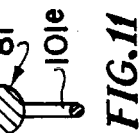

PLACEMENT TOOL AND METHOD FOR LAPAROSCOPIC HERNIA REPAIR

This application is a continuation-in-part of application Ser. No. 07/968,551 filed on Oct. 29, 1992, now abandoned.

This invention relates to a tool for the placement of mesh and method in a laparoscopic procedure and a method for making the tool.

In certain laparoscopic procedures, for example, for hernia repair it is common to utilize mesh in connection with such hernia repair. Typically, at the present time, a prosthetic mesh is put in place in a laparoscopic procedure by first rolling the mesh into a roll which has an appearance similar to a cigarette and then pushing this roll through a cannula with laparoscopic forceps into the abdominal space of the patient. The roll of mesh is then manipulated to unroll the roll and place the material in the desired location utilizing other laparoscopic instruments. During such manipulative steps, it has been found that the mesh which is to be used for the hernia graft has a tendency to adhere to the tissue within the abdominal cavity which makes it cumbersome, difficult and time consuming to position the mesh in the desired location. In co-pending application Ser. No. 07/893,988, filed Jun. 2, 1992, there is disclosed certain mesh conformations and delivery means for delivering the same into the abdominal cavity. However, it has been found that even such grafts and the method for placing of same is not adequate for relatively large rectangular sheets of mesh material such as may be typically used in bilateral hernia repair. There is, therefore, a need for a new and improved tool for the placement of mesh in laparoscopic procedures.

In general, it is an object of the present invention to provide a placement tool for mesh and method in laparoscopic procedures which makes possible the expeditious placement of mesh.

Another object of the invention is to provide a tool and method of the above character which permits the placement of relatively large sheets of mesh.

Another object of the invention is to provide a tool and method of the above character which makes it possible to place customized sheets of mesh.

Another object of the invention is to provide a tool and method of the above character which permits placement of the mesh in a short period of time.

Another object of the invention is to provide a tool and method of the above character in which the mesh can be readily positioned in the desired location without adhering to tissue before it reaches the desired location.

Another object of the invention is to provide a tool of the above character which can be operated by one hand of the physician or surgeon.

Additional objects and features of the invention will appear from the following description in which the preferred embodiment is set forth in detail in conjunction with the accompanying drawings.

FIG. 1 is a side elevational view of a placement tool for mesh incorporating the present invention and having the mesh partially extending therefrom.

FIG. 2 is a cross-sectional view of the tool shown in FIG. 1.

FIG. 3 is a cross-sectional view taken along the line 3—3 of FIG. 1.

FIG. 4 is a cross-sectional view taken along the line 4—4 of FIG. 2.

FIG. 5 is a cross-sectional view taken along the line 5—5 of FIG. 2.

FIG. 6 is a cross-sectional view taken along the line 6—6 of FIG. 2.

FIG. 7 is a side elevational view partially in cross section of another embodiment of a placement tool for mesh incorporating the present invention and having the mesh partially extending therefrom.

FIG. 8 is a cross-sectional view taken along the line 8—8 of FIG. 7.

FIG. 9 is a cross-sectional view taken along the line 9—9 of FIG. 7.

FIG. 10 is a partial side elevational view of the distal extremity of the rod provided in the placement tool as shown in FIG. 7.

FIG. 11 is a cross-sectional view taken along the line 11—11 of FIG. 10.

FIG. 12 is a partial isometric view partially in cross section showing the method by which a precise bore can be formed in the placement tool.

FIG. 13 is a cross-sectional view taken along a line 13—13 in FIG. 12.

FIG. 14 is a side elevational view of the placement tool shown in FIG. 7 disposed in an introducer.

FIG. 15 is a partial side elevational view with certain portions being in cross section of another embodiment of a placement tool incorporating the present invention.

FIG. 16 is a view looking along the line 16—16 of FIG. 15.

FIG. 17 is a cross-sectional view taken along the line 17—17 of FIG. 15.

In general, the placement tool of the present invention is for placement of a sheet of mesh material having at least first and second edges and having a width between the edges in a laparoscopic procedure in a patient utilizing a cannula having a passage therein, comprising an elongate relatively rigid tubular member having proximal and distal extremities with the distal extremity adapted to be introduced through the cannula, said elongate tubular member having a bore extending therethrough. A rod is disposed in the bore in the tubular member and has proximal and distal extremities with the distal extremity terminating short of the distal extremity of the elongate tubular member. A rotatable member is secured to the proximal extremity of the rod. Handle means is provided which is adapted to be grasped by human hands. The handle means is secured to the proximal extremity of the elongate tubular member and receives the rotatable member. The handle means has at least one opening therein in registration with the rotatable member and is adapted to receive a finger of the human hand for engaging the handle means for rotation of the rotatable member and the rod carried thereby with a finger of the same hand grasping the handle means. A sleeve is disposed over the tubular member and has a distal extremity which has an inside diameter which is substantially greater than the outside diameter of the rod to form a cylindrical storage chamber. The distal extremity of the sleeve has a slot therein which extends longitudinally of the sleeve permitting access to the distal extremity of the rod. Means is carried by the distal extremity of the rod for engaging one edge of the sheet of mesh so that the sheet of mesh can be wrapped about said rod in one direction by rotation of said rotatable member and brought into said storage chamber so that all of the sheet of mesh is within the storage chamber to facilitate introduction of the distal extremity of the elongate tubular member into the cannula. This sheet of mesh is dischargeable from the storage chamber by rotation of the rotatable member and the rod carried thereby in an opposite direction to cause the other edge of the sheet of material which is free of the rod to move through the slot and out of said storage chamber to permit the sheet of mesh to be grasped and placed within the patient during the laparoscopic procedure. Alternatively, the sheet of mesh can be pushed off of the rod and out of the storage chamber.

More, in particular, as shown in FIGS. 1–6 of the drawings, the placement tool 11 incorporating the present invention consists of a tubular assembly 12 having proximal and distal extremities 13 and 14. The tubular assembly 12 consists of a relatively rigid elongate tubular member 16 formed of a suitable polymeric material such as polyvinylchloride which has proximal and distal extremities 17 and 18. It is provided with a bore 19 which extends from the proximal extremity to the distal extremity and opens into a smaller bore 21. The tubular member 16 can be opaque if desired. The tubular assembly 12 also includes a sleeve or sheath 22 which extends co-axially of the tubular member 16 and is formed of a less rigid and slightly bendable material such as polyethylene which is also substantially transparent. It has a proximal extremity 23 which is coextensive with the proximal extremity 17 of the tubular member 16. It is provided with a distal extremity 24 which extends substantially beyond the distal extremity of 18 of the tubular member 16. The distal extremity 24 has a bore 25 which is in communication with the bore 21.

The tubular assembly 12 can have a suitable length as, for example, 20 centimeters with the tubular member 16 having a length of 22 centimeters and the sleeve 22 having a length of approximately 6 centimeters which extends beyond the distal extremity 18 of the tubular member 16. The tubular member 12 can have an exterior diameter of 10 millimeters with the sleeve or sheath 22 having a wall thickness of 1 centimeter and the tubular member 16 having a wall thickness of 2 millimeters so that the bore 19 has a diameter of 4 millimeters.

An elongate cylindrical rod 26 is disposed within the bore 21 and the bore 25 and extends longitudinally thereof. The rod 26 has proximal and distal extremities 27 and 28. It can be formed of a suitable material such as stainless steel. The rod 26 extends through the bore 21 and has its distal extremity 28 terminating just short as, for example, by 3 millimeters from the distal extremity 24 of the sleeve 22. The rod 26 has a suitable outside diameter such as 3 millimeters so that an annular chamber or recess 29 is formed between the rod 26 and the interior surface of the bore 25 of the sleeve 22. A rotatable member 31 is provided which is generally cylindrical in shape and can be formed of a suitable material such as plastic. The rotatable member 31 is mounted on the proximal extremity of the rod 27 and is secured thereto so that, as the rotatable member 31 is rotated, the rod 26 will rotate therewith. The exterior surface of rotatable member 31 can be knurled as shown to facilitate grasping by a finger of a hand as hereinafter described.

Handle means 36 is provided adapted to be grasped by the human hand and consists of a cylindrical member 37 formed of a suitable material such as plastic which is sized so it can readily accommodate an adult human hand and by way of example has a suitable outside diameter as, for example, approximately 2 centimeters and a length of 11 centimeters. It can be solid, however, as shown it can also be hollow. The handle means 36 also includes a sleeve 38 formed of a suitable material such as plastic which has a tapered end 39 that receives the proximal extremity 13 of the tubular assembly 12. The proximal extremity 13 is retained therein by suitable means such as an adhesive (not shown). The sleeve 38 is provided with first and second diametrically spaced apart openings 41 and 42 which overlie the rotatable member 31 but has a length which is slightly less than the length of the rotatable member 31. The rotatable member 31 is seated in circular recesses 43 and 44. The recess 44 is formed by the cylindrical member 37 being seated within the sleeve 38 and being retained therein by suitable means such as a set screw 46. The sleeve 38 is provided with inclined surfaces 47 and 48 at opposite ends of the openings 41 and 42 to facilitate the finger of a hand moving into the openings 41 and 42.

The distal extremity of the tubular assembly 12 is provided with an elongate slot 51 which is formed in the distal extremity 24 of the sleeve 22 and subtends an angle of approximately 90° as shown in FIG. 3, the slot permits access to the chamber or recess 29 and the distal extremity 28 of the rod 26.

The tool 11 is adapted to be used for placement of a sheet 56 of mesh of a suitable medical grade material which has been cut to the desired shape by the physician to provide a graft mesh 56 which has first and second spaced apart edges 57 and 58 which as shown may be generally parallel to each other. The sheet 56 is provided with a width so that it has third and fourth edges 59 and 61 which extend in a direction generally perpendicular to the first and second edges 57 and 58.

Means is provided on the distal extremity 28 of the rod 26 to secure one of the edges 57 and 58 of the sheet 56 to the same. Thus, there has been provided a slit 66 in the distal extremity 28 extending longitudinally inwardly from the distal extremity of the rod 26 to a point which is proximal to the distal extremity 18 of the tubular member 16. The slot 51 provided in the tubular assembly 12 can have a suitable length as, for example, 65 millimeters and a width of 8 millimeters. The slit 66 can have a similar length of approximately 62 millimeters and a width of 1 millimeter less. Thus, there are provided two tines 67 and 68 on the distal extremities 28 of the rod 26, the distal extremities of which are rounded and slightly bowed outwardly with respect to each other to provide a fork-like construction. By rotation of the rod 26, the slit 66 between the tines 67 and 68 can be rotated so that the slit 66 is directly opposite the slot 51 in the sheath 22.

The tines 67 and 68 are in substantial yieldable spring-like contact with each other throughout their length, except at the proximal extremities where they are splayed outwardly to facilitate loading the mesh therein as hereinafter described.

Let it be assumed that it is desired to utilize the tool and method of the present invention for the placement of a sheet of mesh material 56 in a laparoscopic procedure utilizing a cannula (not shown) having a bore or passage therein. Let it also be assumed that the surgeon has cut the sheet of mesh 56 to the appropriate size as, for example, a sheet of mesh having a suitable length as, for example, 15 centimeters and a width of 7 centimeters. One of the edges as, for example, edge 57 is taken by the fingers of one hand while holding the handle means 36 in the other hand and the edge 57 is introduced through the slot 51 in the sleeve 22 and slid into the slit 66 between the splayed ends of the tines 67 and 68. The edge 57 is pushed inwardly into the chamber until that edge 57 is seated within the slit 66 and is frictionally retained therein. The rotatable member 31 can then be rotated by one or more fingers of the same hand holding the handle means as, for example, the thumb and forefinger and rotating it in either a clockwise or counter-clockwise direction. Thus the sheet of mesh 56 can be wrapped into the chamber 52, in either a clockwise or counter-clockwise direction as indicated by the arrow 70 in FIG. 3. The direction in which the mesh is rolled into the chamber is determined by the surgeon during the surgical procedure based on the assessment of the anatomic location and the direction in which the mesh graft is to be placed in the surgical procedure. The surgeon continues rotating the of rotatable member 31 by the fingers of the hand to cause the mesh 56 to be rolled up on the rod 26 into a compact roll as shown in FIG. 3 until the other end of the mesh 58 is brought into the chamber 52. The sheet of mesh 58 is then firmly retained within the chamber 52 and is protected by the distal extremity 24 of the sleeve 22.

After the sheet 56 of the mesh has been loaded into the chamber 52, the tool 11 can be taken and the distal extremity 14 can be inserted into a cannula (not shown) being utilized in the laparoscopic procedure in a body having tissue. After the distal extremity 14 of the tool 11 has been positioned in the abdominal cavity and the distal extremity has been positioned in the desired location for the proper location of the sheet of mesh, the surgeon holding the tool in one hand uses the thumb and forefingers of the hand to rotate the rotatable member 31 and the rod 26 carried thereby in the opposite direction from which the mesh was rolled into the chamber 52 to cause the edge 58 to exit through the slot 51 from the chamber 52. Thereafter, the edge 58 can be grasped by laparoscopic forceps and the remainder of the material unrolled from the chamber 52 till the mesh has been discharged or removed from the chamber. As the mesh is unrolled over the desired area of the tissue, it can be progressively tacked down to the tissue, as for example to the fascia and Cooper ligament with a stapler (not shown). After the placement of the mesh, the tool can then be removed and the laparoscopic procedure completed.

It can be seen by the use of the tool 11, a sheet of mesh for the graft can be of various sizes and can be readily placed in the abdominal cavity. The placement can take place without the mesh coming in contact with tissue before it is placed. The placement of the mesh can be readily controlled in an expedient manner with a minimal use of time.

Another embodiment of a placement tool 71 incorporating the present invention is shown in FIGS. 7–11 and consists of a tubular assembly 72 having proximal and distal extremities 73 and 74. The tubular assembly 72 consists of a tubular member 76 of the same type as tubular member 16 described in the previous embodiment. The tubular member 76 is provided with a centrally disposed bore 77 extending from the proximal extremity 73 to the distal extremity 74. A sleeve or sheath 78 extends coaxially over the tubular member 76 and is of the same type as the sleeve or sheath 22 described in the previous embodiment. The distal extremity of the sleeve or sheath 78 extends beyond the distal extremity of the tubular member 76 and has a bore 79 therein which is in communication with the bore 77.

An elongate cylindrical rod 81 is disposed within the bore 79 and the bore 77 and extends longitudinally thereof. Also it is formed in the manner similar to the rod 26 hereinbefore described and forms an annular chamber 82 between the rod 81 and the bore 79. A rotatable member 86 similar to the rotatable member 31 is provided which is secured to the proximal extremity of the rod 81 by a suitable means such as a set screw 87. A handle 91 is provided which is secured to the proximal extremity 73 of the tubular assembly 72 and is provided with diametrically spaced-apart openings 92 which expose the rotatable member 86 so that it can be grasped by the fingers of the hand in the same manner as the handle means 36 hereinbefore described.

The rod 81 is provided with a distal extremity which is shown in FIG. 10. The distal extremity of the sleeve or sheath 78 is provided with a slot 96 extending longitudinally thereof corresponding to the slot 51 hereinbefore described which gives access to the chamber 82. Means is provided on the distal extremity of the rod 81 for engaging one edge of a sheet of mesh so that the sheet of mesh can be wrapped about the rod in one direction by rotation of the rotatable member 86 and consists of at least one outwardly bowed spring member 101. The spring member 101 as shown in FIG. 10 is comprised of a single length of a steel spring wire which has ends 101a and 101b. The spring wire 101 is threaded through three holes 102, 103 and 104 spaced-apart longitudinally of the rod 81 and extending diametrically therethrough. The wire forming the spring member 101 has its end 101a threaded through the hole 102 and its end 101b threaded through the hole 103 to provide a first outwardly bowed portion 101c and, then through hole 104 to provide another outwardly bowed portion 101d, back through the hole 103 to provide another outwardly bowed portion 101e, and then back through the hole 102 to provide the outwardly bowed portion 101f and to have end portion 101b just beyond the hole 102. Thus, as shown in FIGS. 10 and 11 there are provided two diametrically opposed outwardly bowed portions which have a diameter which is approximately as great and preferably slightly greater than the inner diameter of the chamber 82.

Operation and use of the placement tool 71 in placing a graft mesh 56 of the type hereinbefore described can now be briefly described as follows. Let it be assumed that the graft mesh 56 has been cut in the manner hereinbefore described and that the first edge 57 has been introduced into the slot 96. The rotatable member 86 can be rotated either in a clockwise or a counterclockwise direction so that at least one of the outwardly bowed portions of the spring member 101 engages the first edge 57 to rotate the free edge 57 into the chamber 82. As this is occurring, the spring member portion is canted sideways against the yieldable force of the spring member 101 to drag the free end 57 inwardly into the chamber 82 against the smooth inner surface of the sleeve 78. Continued rotation of the rotatable member 86 in the same clockwise direction causes additional portions of the graft mesh 56 to be drawn into the chamber and to be frictionally retained therein as shown particularly in FIG. 9.

When substantially all of the mesh 56 has been loaded into the chamber 82, the distal extremity 74 of the tubular assembly 72 can be introduced into a cannula (not shown) being utilized in a laparoscopic procedure as hereinbefore described. When it is desired to unload the mesh graft 56 during the laparoscopic procedure, it is merely necessary to rotate the member 86 in the opposite direction, as for example in a counterclockwise direction to dispense the graft 56 through the slot 57 and to eventually release the end 57 of graft mesh. Because of the canting of the bowed portions 101e, 101d, 101f and 101c, the mesh graft will be firmly retained and will be dispensed out through the slot 96 until the free end 57 passes out of the slot 96.

As hereinbefore explained, the spring member 101 is formed so that it is only slightly less in diameter than the inner surface of the sleeve 78 so that the spring members will not engage with the slot 96 as the rotatable member 96 is rotated. However, the spring member 101 should be of a diameter so that only graft mesh 56 is placed in the slot 57, the bowed portions of the spring member 101 will be canted in a counterclockwise direction when the rod 81 is rotated in a clockwise direction and conversely will be canted in a clockwise direction when the rod 81 is rotated in a counterclockwise direction. The roughness of the graft mesh 56 facilitates grasping of the same by the bowed portions of the spring member 101.

A particularly unique method has been provided for forming a precise bore 77 in the tubular member 76 so that the rod 81 can extend therethrough and smoothly rotate therein. This is accomplished by forming the tubular member 76 in one piece in an injection mold which heretofore would have been difficult if not impossible to accomplish. This is made possible by the use of a two-part mold 111, illustrated in FIG. 12, consisting of an upper part 111a and a lower part 111b which are separable along a parting line 112. The top part 111a is provided with spaced-apart recesses 116 semicircular in cross section extending longitudinally of the upper part and into which there radially extends spaced-apart protrusions 117 having semicircular portions 117a which have as their centers, the centers of semicircular recesses 116. The protrusions 117 have a length which is approximately one-half of the length of the recess 116. Similarly, the lower part 111b is provided with spaced-apart recesses 118 semicircular in cross section extending longitudinally thereof and which underlies the recess 116. The lower part 111b is provided with spaced-apart protrusions 119 which extend radially and longitudinally of the recesses 118 and is provided with semicircular portions 119a having as their centers, the centers of the recesses 118.

As shown particularly in FIG. 12, the protrusions 117 and 118 are formed so that they have a length permitting one protrusion to extend beyond the other to provide overlaps of the two protrusions corresponding to the semicircular portions 117a and 119a which corresponds to the circle which is the diameter of the bore 79 provided in the sleeve or sheath 78. The semicircular portion 117a and 119a touch each other so that when molten plastic is introduced into the mold 111 it will form the tubular member 76 with the bore 77 extending therethrough merely leaving longitudinally offset slots 121 and 122 which are covered up by the sleeve or sheath 78. If still greater precision is provided for rotation of the rod 81 in the bore 77, bearings (not shown) can be provided in the proximal extremities of the bore 77 which can be engaged by the rod 81.

In FIG. 14, the tool 71 is shown disposed in a an introducer 131 of the type typically used with a trocar for making the initial penetration through tissue, as for example through the abdominal wall of a patient. The introducer 131 is of a conventional type and includes a elongate tubular member 132 which is sized so that it can accommodate the tool 71. It is provided with a flanged fitting 133 which has an on/off valve 134 mounted thereon. After tool 71 has the mesh 56 rolled into the chamber 82, the tool can be introduced through the introducer 131 into the cavity in the body into a position such as shown in FIG. 14. Thereafter, the mesh 56 can be discharged from the placement tool by first advancing a small part of the mesh 56 out of the slot 96 and then pulling proximally on the tool 71 so that the mesh 56 engages the distal extremity of the tubular member 132 of the introducer 131 to cause the mesh 56 to be pushed through the slot 96 so that the entire roll of mesh 56 can be discharged as a roll. Thereafter the mesh 56 can be unrolled and distributed by other tools (not shown) utilized during the laparoscopic procedure. In this way, it can be seen that mesh 56 can be discharged from the placement tool in a very short period of time in one motion without spending time unrolling the mesh 56 in its entirety through the slot 96.

It should be appreciated that this push off technique for the mesh 56 can be utilized with the spring member 101 hereinbefore described with the slit 66 provided in the distal extremity of the rod 26. In both cases the mesh 56 can be pushed off of the spring member 101 or alternatively pushed out of the slit 66.

Still another embodiment of a placement tool 141 incorporating the present invention is shown in FIGS. 15–17 and consists of a tubular assembly 142 on which there is mounted a handle 146. The tubular assembly 142 consists of a tubular member 147 which is slidably mounted in a sleeve 148 secured to the handle 146. The distal extremity of the sleeve 148 is provided with a slot 149 which is open at its distal extremity. A rod 151 is rotatably mounted in the tubular member 147 and is secured to a rotatable member 152 of the type hereinbefore described that is accessible through diametrically opposed slots or openings 153 in the handle 146. The distal extremity of the rod 151 is provided with means (not shown) such as the slit 66 or the spring member 101 hereinbefore described in conjunction with the previous embodiments for receiving the mesh 56.

Means is provided for moving the tubular member 147 relative to the rod 151 and consists of a pair of radially extending ears 156 formed integral with the proximal extremity of the tubular member 151 and which extend through diametrically opposed slots 157 provided in the handle 146. As can be seen from FIG. 15, the ears 156 have a length such that they extend outwardly beyond the outer confines of the handle 146 so they can be grasped by two fingers of the hand grasping the handle 146. Thus, they can be used for moving the tubular member 147 longitudinally over the rod 151 to push the mesh 56 off the means carried by the distal extremity of the rod for retaining the mesh so that the mesh can be rapidly discharged from the placement tool after it has been introduced into the cavity in which it is to be disposed. With such an arrangement, it is not necessary that any of the mesh 56 be enrolled through the slot 149. The slidably movable tubular member 147 engages the proximal extremity of the rolled mesh 56 and merely pushes it off of the rod so that with one movement of the fingers, the mesh can be discharged from the placement tool. The mesh can then be unrolled and placed in a conventional manner.

From the foregoing, it can be seen that the tool 11 of the present invention has a number of advantages. The concentric rotation of the knob or rotatable member 51 makes possible a one-handed operation of the tool. The mesh for the graft can be rolled in either a clockwise or a counterclockwise direction. The means provided at the distal extremity of the tool engaging the mesh facilitates directional control in dispensing of the mesh from the tool. The mesh material is compacted as it is rolled into the device making it possible to use a relatively long length of mesh as for example as is often used in bilateral hernia repair. Since the mesh is covered by the tool during introduction, there is minimal premature adherence to the surrounding tissue. The tool is also constructed in such a manner so that there is a minimal leakage of $CO_2$ used for insufflation from the abdominal cavity during placement of the mesh. These same features are also present with the placement tool 71 and 141 also described. The additional embodiments of the placement tool have the advantage in that means is provided permitting rapid removal of the mesh from the tool when that is desired merely by making it possible to push the rolled mesh out of the tool by movement of the tool relative to an introducer device or by utilizing a slidably mounted tubular member in the tool itself for pushing the rolled mesh out of the placement tool. Also there is provided means for making it possible to provide a precision bore in a tubular member carrying the rotatable rod on which the mesh is rolled.

What is claimed is:

1. A tool for the placement of a sheet of mesh material having first and second edges and a width between the edges in a laparoscopic procedure in a patient utilizing a cannula having a bore therein comprising: an elongate tubular assembly having proximal and distal extremities, the distal extremity adapted to be introduced through the cannula, said elongate tubular assembly including an elongate tubular member having a bore, a rod disposed in the bore of the elongate tubular member and having an outer diameter and having a proximal extremity and a distal extremity with the distal extremity of the rod terminating short of the distal extremity of the elongate tubular assembly, a rotatable member secured to the proximal extremity of the rod, handle means adapted to be grasped by a human hand and secured to the proximal extremity of the elongate tubular assembly and receiving said rotatable member, said handle means having at least one opening therein overlying the rotatable member and adapted to receive a finger of the human hand grasping the handle means for rotating the rotatable member and the rod carried thereby, a sleeve disposed over said elongate tubular member and having a distal extremity which has an inside diameter substantially greater than the outside diameter of the rod to form an annular chamber, said sleeve having a slot therein extending longitudinally of the elongate tubular assembly which permits access to the annular chamber and the distal extremity of the rod, means carried by the distal extremity of the rod for engaging one of said edge of said sheet of mesh so that as the rod is rotated said sheet of mesh is wound about said rod in one direction and brought into and stored as a roll in said annular chamber to permit introduction of the distal extremity of the elongate tubular assembly with the sheet of mesh stored therein through the cannula, said sheet of mesh being dischargeable from the chamber by rotation of the rod in an opposite direction to cause the other edge of said sheet of mesh to move through said slot and out of said annular chamber to permit the sheet of mesh to be placed within the patient during the laparoscopic procedure.

2. A tool as in claim 1 wherein said means carried by the distal extremity of the rod includes a slit formed in said rod, said slit extending from the distal extremity of the rod and extending longitudinally of the rod to form first and second tines having distal extremities.

3. A tool as in claim 1 wherein the distal extremities of the tines yieldably frictionally engage each other and are splayed outwardly at their distal extremities to facilitate loading of said sheet of mesh material into the slit between the tines.

4. A tool as in claim 1 wherein said sleeve is formed of a deformable material.

5. A tubular member as in claim 4 wherein said sleeve is formed of a substantially transparent material.

6. A tool as in claim 1 wherein said handle means includes a sleeve having one end secured to the proximal extremity of the elongate tubular assembly, said sleeve having a cylindrical recess therein receiving said rotatable member, said sleeve having formed therein two openings accessible to the fingers of the hand holding the handle means and overlying the rotatable member and wherein said handle means includes a cylindrical handle member disposed on the other end of said sleeve and retaining said rotatable member in said sleeve.

7. A tool as in claim 6 wherein said cylindrical handle member extends proximally of the rotatable member.

8. A tool as in claim 1 wherein said means carried by the distal extremity of the rod includes outwardly bowed radially extending spring members disposed in the annular chamber.

9. A tool as in claim 8 wherein said spring members extend substantially the entire length of the slot in the sleeve assembly.

10. A tool as in claim 1 wherein said elongate tubular member is slidably mounted in said sleeve, and further comprising means carried by the handle means and the elongate member for permitting movement of the elongate tubular member relative to the rod so that the elongate tubular member can be used for pushing the rolled mesh off of the rod.

11. A tool as in claim 10 wherein said means carried by the handle and the elongate tubular member for causing movement of the elongate tubular member with respect to the rod includes means having a longitudinally extending slot formed in the handle and an upstanding ear secured to the elongate tubular member and extending through the longitudinally extending slot and adapted to be grasped by a finger of the hand holding the handle means.

12. A tool for the placement of flexible sheet material having first and second edges and a width between the edges in a laparoscopic procedure in a patient utilizing a cannula having a bore therein, comprising an elongate tubular assembly having proximal and distal extremities and having the distal extremity adapted to be introduced through the cannula, a handle mounted on the proximal extremity of the elongate tubular assembly, the elongate tubular assembly including a sleeve having a proximal extremity and a distal extremity, the distal extremity of the sleeve having an end, said proximal extremity of said sleeve being attached to said handle, a rod disposed in the sleeve and having a proximal extremity and a distal extremity, means carried by the handle for rotating the rod in clockwise and counterclockwise directions, said sleeve having an internal diameter which is greater than the outside diameter of the rod to form an annular chamber within the sleeve, said sleeve having a slot therein extending longitudinally of the sleeve through the end of the sleeve, said slot in said sleeve having a width which subtends an angle of approximately 90 degrees providing access to and from the annular chamber and the distal extremity of the rod, means carried by the distal extremity of the rod for gripping the first edge of the sheet so that as the rod is rotated in one of said clockwise and counterclockwise directions said sheet is wound about said rod and the second edge is brought into said annular chamber to store the sheet in a roll in the annular chamber whereby the distal extremity of the tubular assembly with the sheet stored therein can be introduced through the cannula into the patient, the width of the slot permitting the sheet to be dischargeable through said slot by rotation of said rod in the other of said clockwise and counterclockwise directions.

13. A tool as in claim 12 wherein said elongate tubular assembly further includes an elongate tubular member, the sleeve extending over and distally beyond the elongate tubular member, the elongate tubular member being slidably mounted with respect to said rod, means carried by the handle for causing slidable movement of the elongate tubular member with respect to the rod so that the sheet rolled onto the rod in the annular chamber can be pushed off of the rod by the elongate tubular member.

14. A tool as in claim 12 wherein said means carried by the distal extremity of the rod for grouping the first edge of the sheet includes a slit formed in the rod extending from the distal extremity of the rod and extending longitudinally of the rod.

15. A tool for the placement of flexible sheet material having first and second edges and a width between the edges in a laparoscopic procedure in a patient utilizing a cannula having a bore therein, comprising an elongate tubular assembly having proximal and distal extremities and having the distal extremity adapted to be introduced through the cannula, a handle mounted on the proximal extremity of the elongate tubular assembly, the elongate tubular assembly including an elongate tubular member having a bore extending longitudinally thereof and a sleeve extending over the elongate tubular member and having a proximal extremity and a distal extremity, said distal extremity of said sleeve extending beyond the distal extremity of the elongate tubular member, said proximal extremity of said sleeve being attached to said handle, a rod disposed in the bore in the elongate tubular member and having a proximal extremity and a distal extremity with the distal extremity terminating short of the distal extremity of the sleeve, means carried by the handle for rotating the rod in clockwise and counter-clockwise directions, said sleeve having an internal diameter which is greater than the outside diameter of the rod to form an annular chamber within the sleeve, said sleeve having a slot therein and extending longitudinally of the sleeve permitting access to the annular chamber and the distal extremity of the rod, means carried by the distal extremity of the rod for engaging one edge of the sheet so that as the rod is rotated said sheet is wound about said rod in one direction and brought into and stored as a roll in said annular chamber permitting the distal extremity of the tubular assembly with the sheet stored therein to be introduced through the cannula, said means carried by the distal extremity of the rod for engaging one end of the sheet including a radially extending spring member secured to the rod and disposed within the annular chamber.

16. A tool as in claim 15 wherein said radially extending spring member extends substantially the entire length of the slot in the sleeve.

17. A tool as in claim 15 wherein said handle includes means for providing access to the means for rotating the rod so that the means for rotating the rod can be engaged by the fingers of the hand to rotate the rod.

18. A method for placement of a flexible sheet having first and second edges in a laparoscopic procedure into a cavity in a body having tissue utilizing a tool having a sleeve with a distal extremity with a chamber therein and a slot extending through the distal extremity and providing access to the chamber and a cannula, comprising taking the first edge of the sheet and introducing it through the slot, wrapping the sheet into a roll by taking the first edge which has been introduced through the slot and rotating the first edge to bring the sheet of mesh into the chamber until the entire sheet of mesh is formed into a roll in the chamber, introducing the tool through the cannula into the cavity in the body and discharging the sheet from the chamber by partially unrolling the roll so that the second edge of the sheet exits through the slot and retracting the tool to cause the sheet to be engaged by the cannula and to be pushed out of the chamber of the tool by relative movement between the tool and the cannula.

19. A method for placement of a flexible sheet having first and second edges in a laparoscopic procedure into a cavity in a body having tissue utilizing a tool having a sleeve with a distal extremity with a chamber therein and a circumferentially wide slot extending through the distal extremity and providing access to and from the chamber, comprising: taking the first edge of the sheet and introducing it through the slot, wrapping the sheet into a roll by taking the first edge which has been introduced through the slot and rotating the first edge in a first angular direction to bring the sheet of mesh into the chamber until the entire sheet of mesh is formed into a roll in the chamber, introducing the tool into the cavity in the body, orienting the sleeve so that the slot faces in a desired direction and discharging the sheet from the chamber by rotating the second edge of the sheet in a second angular direction so as to cause the second edge to find by itself the slot in the sleeve and to move into the slot in the sleeve and thus exit through the slot in the sleeve in the desired direction and unwrap the sheet.

20. A method as in claim 19 wherein the step of discharging the sheet from the chamber is facilitated by the circumferentially wide slot subtending an angle of approximately 90 degrees.

\* \* \* \* \*